(12) United States Patent
Feugier (10) Patent No.: US 7,374,940 B2
(45) Date of Patent: May 20, 2008

(54) METHOD AND APPARATUS FOR DETERMINING THE PROGRESS OF A URANIUM OXYFLUORIDE CONVERSION REACTION IN A FURNACE AND FOR CONTROLLING THE REACTION

(75) Inventor: André Feugier, Chatuzange le Goubet (FR)

(73) Assignee: Societe Franco-Belge de Fabrication de Combustible-FBFC, Courbevoie (FR)

( * ) Notice: Subject to any disclaimer, the term of this patent is extended or adjusted under 35 U.S.C. 154(b) by 827 days.

(21) Appl. No.: 10/203,445

(22) PCT Filed: Feb. 9, 2001

(86) PCT No.: PCT/FR01/00391

§ 371 (c)(1),
(2), (4) Date: Aug. 8, 2002

(87) PCT Pub. No.: WO01/58810

PCT Pub. Date: Aug. 16, 2001

(65) Prior Publication Data

US 2003/0064519 A1 Apr. 3, 2003

(30) Foreign Application Priority Data

Feb. 11, 2000 (FR) .................................. 00 01756

(51) Int. Cl.
*G01N 1/26* (2006.01)
*G01N 1/22* (2006.01)
*G01N 33/00* (2006.01)
*C01G 43/00* (2006.01)

(52) U.S. Cl. .................. 436/34; 73/863.11; 73/863.31; 73/863.81; 73/863.86; 73/864.73; 138/113; 422/62; 422/83; 422/159; 422/209; 422/213; 423/253; 423/258; 423/260; 423/261; 436/101; 436/103; 436/136

(58) Field of Classification Search .................. 423/19, 423/253, 258, 260–261; 422/61–62, 83, 422/142, 145, 159, 209, 213; 73/863.86, 73/863.11, 863.31, 863.81–863.82, 864.73–864.74; 436/38, 54, 101, 106, 136, 34; 138/113
See application file for complete search history.

(56) References Cited

U.S. PATENT DOCUMENTS 2,030,682 A * 2/1936 Campbell ................. 73/863.23
(Continued)

FOREIGN PATENT DOCUMENTS

CS 146754 * 12/1972
(Continued)

OTHER PUBLICATIONS

Sanderson, D. K. et al, Energy & Fuels 1993, 7, 910-918.*
(Continued)

*Primary Examiner*—Arlen Soderquist
(74) *Attorney, Agent, or Firm*—Davidson, Davidson & Kappel (57) ABSTRACT

A substance in a condensed state, for example a powdered solid, is in continuous movement in the longitudinal direction (6) of a furnace (4, 5). A reactive gas mixture is brought into contact with the substance in the condensed state. A plurality of samples of the gaseous mixture are removed at a plurality of reference points (14) spaced apart from one another along the longitudinal direction (6) of the furnace (4, 5); each of the gas samples is analyzed outside the furnace to determine the composition of the gas mixture and for each point (14), the extent of a chemical reaction between the condensed substance and the reactive gas mixture is deduced from the composition of the gas mixture at each of the reference points (14). In particular, the apparatus comprises a sampling and injection rod (10) introduced into the furnace (4, 5) and disposed in its longitudinal direction (6). The invention is of particular application to modeling a rotary furnace (4, 5) for converting uranium oxyfluoride into uranium oxides and for controlling the conversion reaction in the furnace (4, 5).

13 Claims, 6 Drawing Sheets

U.S. PATENT DOCUMENTS

| | | | | |
|---|---|---|---|---|
| 2,534,181 | A * | 12/1950 | Roberts | 73/863.33 |
| 3,085,435 | A * | 4/1963 | Miscoe et al. | 374/143 |
| 3,845,193 | A * | 10/1974 | Littlechild et al. | 423/261 |
| 3,871,829 | A * | 3/1975 | Keith et al. | 422/204 |
| 3,888,123 | A * | 6/1975 | Kuntziger et al. | 73/863.11 |
| 4,051,731 | A * | 10/1977 | Bohl et al. | 73/863.33 |
| 4,112,055 | A * | 9/1978 | Artaud | 423/261 |
| 4,397,824 | A * | 8/1983 | Butler et al. | 423/260 |
| 4,403,516 | A * | 9/1983 | Mailliet et al. | 73/863.11 |
| 4,413,533 | A * | 11/1983 | Diesel | 73/863.31 |
| 4,830,841 | A * | 5/1989 | Urza | 423/261 |
| 5,723,100 | A * | 3/1998 | Carter et al. | 423/261 |
| 5,757,087 | A * | 5/1998 | Carter et al. | 423/253 |
| 5,875,385 | A * | 2/1999 | Stephenson et al. | 423/260 |
| 5,955,033 | A * | 9/1999 | Hayes | 422/109 |

FOREIGN PATENT DOCUMENTS

| | | | |
|---|---|---|---|
| DE | 41420 | * | 9/1965 |
| DE | 2301264 | * | 7/1974 |
| DE | 115757 | * | 10/1975 |
| EP | 0 322 481 | | 7/1989 |
| FR | 2 771 725 | | 6/1999 |

OTHER PUBLICATIONS

Ryazantsev, A. N., Sbornik Trudov—Gosudarstvennyi Vsesoyuznyi Nauchno-Issledovatel'skii Institut Stroitel'nykh Materialov i Konstruktsii VNIIstrom im. P .P. Budnikova 1966, 13-24.*

Branch, M. C. et al, Symposium on Combustion, 1973, 14, 967-974.*

Soelberg, N. R. et al, Fuel 1985, 64, 776-781.*

Munn, D., World Cement 1986, 17, 434-440.*

Mureau, P. et al, Recents Progres en Genie des Procedes 1991, 5, 283-288.*

CHeung, S. et al, Proceedings—Institute of Environmental Science 1992, 38$^{th}$, 353-360.*

Ion, S. E. et al, Ceramic Engineering and Science Proceedings 1993, 14, 149-154.*

Mureau, P. et al, Advanced Concepts and Techniques in Thermal Modelling, Proceedings of the Eurotherm Seminar, 36th, Poitiers, Fr., 1996, 165-171; Editor(s): Lemonnier, D. et al; Publisher: Elsevier, Paris, Fr.*

Pre, P. et al, Chemical Engineering Science 1998, 53, 2871-2883.*

Hauser, A. et al, International Cement Journal 1999, 51-55.*

Debacq, M. et al, Recents Progres en Genie des Procedes 1999, 13, 121-128.*

Arakawa, H. et al, Tetsu to Hagane 1963, 49, 1753-1759.*

Knudsen, I. E. et al, U.S. At. Energy Comm. 1963, ReportANL-6606, 44 pages.*

Strausberg, S., U.S. At. Energy Comm. 1965, Report NAA-SR-10485, 26 pages.*

Geiss, V. et al, Journal of the Electrochemical Society 1976, 123, 133-136.*

Moulton, D. S. et al, Report 1979, ANL/CEN/FE-79-12, 41 pages.*

Mu, J. et al, Chemical Engineering Communications 1981, 9, 101-120.*

Iwasaki, M. et al, Journal of Nuclear Science and Technology 1983, 20, 400-404.*

Cundy, V. A. et al, Journal of the Air & Waste Management Association 1991, 41, 1084-1094.*

Lacombe, S. et al, Recents Progres en Genie des Procedes 1993, 7, 55-60.*

Lee, M. et al, Steel Research 1999, 70, 15-21.*

Hauser, A. et al, International Cement Journal 1999, 51-52, 54-55.*

Cundy, V. A. et al, JAPCA 1989, 39, 63-75.*

Database WPI Week 198709 Derwent Publications Ltd., London GB; AN 1987 061716'09 XP002154513 & JP 62 017694 A Jan. 26, 1987, (abstract only).

Patent Abstracts of Japan vol. 1999, No. 1 Jan. 29, 1999 & JP 10 279311 Oct. 20, 1998, (abstract only).

Patent Abstracts of Japan vol. 1998, No. 13 Nov. 30, 1998 & JP 10 227881 Aug. 25, 1998.

* cited by examiner

METHOD AND APPARATUS FOR DETERMINING THE PROGRESS OF A URANIUM OXYFLUORIDE CONVERSION REACTION IN A FURNACE AND FOR CONTROLLING THE REACTION

FIELD OF THE INVENTION

The invention relates to a method and apparatus for determining the progress of a chemical reaction in a furnace and for controlling the reaction. In particular, the invention is applicable to the production of uranium dioxide powder used to manufacture nuclear fuel pellets.

BACKGROUND INFORMATION

In nuclear reactors, for example in pressurized water nuclear reactors, a fuel is used that can be constituted mainly of uranium oxide or of a mixture of uranium oxide and plutonium.

Nuclear fuel, which is enriched in fissile elements, for example in uranium-235 in the case of a fuel constituted by uranium oxide, is generally obtained by a process in which the final enrichment product is constituted by gaseous uranium hexafluoride $UF_6$.

The $UF_6$ is then converted into uranium oxide by oxidation using steam, for example.

Current processes producing the best results for converting uranium hexafluoride into uranium oxide are dry direct conversion processes which are conducted in apparatus comprising, in succession, a reactor provided with means for introducing $UF_6$ and steam into a chamber of the reactor in which uranium oxyfluoride $UO_2F_2$ is formed from the $UF_6$, and a rotary tube furnace in which the solid powdered uranium oxyfluoride $UO_2F_2$ is transformed into uranium oxide, the tube furnace being provided with heater means and means for introducing steam and hydrogen via the outlet portion of the rotary furnace as a counter-current to the powdered solid moving in the longitudinal direction of the furnace.

Uranium oxide powder principally constituted by the dioxide $UO_2$ is recovered from the outlet of the rotary furnace, that powder then being conditioned in a conditioning unit before being used to produce sintered nuclear fuel pellets.

The process for transforming uranium oxyfluoride $UO_2F_2$ into uranium oxide is carried out by bringing a powdered solid into contact with a reactive gas mixture containing steam and hydrogen in particular.

Hydrofluoric acid HF is formed in the rotary furnace by oxidizing the sulfur oxyfluoride with steam.

The solid material circulating in the rotary furnace coming into contact with the reactive gas mixture is the seat of various chemical reactions that result in the formation of uranium oxide, and principally of the dioxide $UO_2$; in particular, the chemical reactions indicated below occur:

$UO_2F_2+H_2O \rightarrow UO_3+2HF$ $3UO_3 \rightarrow U_3O_8+½O_2$ $U_3O_8+2H_2 \rightarrow 3UO_2+2H_2O$ Thus, the composition of the continuously moving solid material in the furnace and the composition of the reactive gas mixture vary essentially in the longitudinal direction of the furnace along which the powdered solid material moves, with the gas mixture moving as a counter-current.

In order to control the chemical reactions in the furnace to the best possible extent, the heater elements of the furnace disposed at the periphery of the jacket of the rotary furnace are adjusted to obtain a regular temperature distribution in the longitudinal direction of the furnace.

However, that method of adjusting the temperature in the longitudinal axial direction of the furnace cannot effectively control the composition of the uranium oxides at the furnace outlet.

Adjusting the flow rates of the hydrogen and steam introduced via the outlet end portion of the rotary furnace cannot improve control of the conversion reactions in the furnace because the reactive gases are diluted in the furnace and because of the random nature of the distribution of the reactive gases obtained inside the furnace chamber.

Further, uranium dioxide $UO_2$ can be produced from the oxide $U_3O_8$ via intermediate reactions during which different uranium oxides are obtained in accordance with the transformation sequence $U_3O_8 \rightarrow U_3O_7 \rightarrow U_4O_9 \rightarrow UO_2$.

In general, no method is known for determining how the reactions between the reactive gas mixture and the oxyfluoride or uranium oxides moving along the rotary furnace are progressing in the longitudinal direction of movement of the substances inside the rotary furnace. Access to a graph of the progress of the reactions inside the rotary furnace would mean that the reactions could be manipulated to optimize the conversion process to obtain oxides with the desired composition at the furnace outlet.

In particular, in order to obtain green pellets with very high mechanical strength as measured by crush, microhardness or wear tests in which the uranium oxide powder is compressed, it has been observed that it is necessary to use oxide powders of a composition such that the atomic ratio of the oxygen over the uranium (O/U) is substantially higher than the ratios normally obtained with oxides from the outlet of a uranium oxyfluoride converting furnace, which oxides are constituted principally by uranium dioxide $UO_2$.

To increase the O/U ratio, mixing certain proportions of particles of uranium dioxide $UO_2$ obtained by dry conversion with particles of an oxide such as $U_3O_8$ has been proposed, for example. That method, which can increase the O/U ratio of the oxides used to produce fuel pellets, necessitates oxidizing the uranium oxide $UO_2$ under perfectly controlled conditions in order to obtain the oxide $U_3O_8$, and then forming a homogeneous mixture of $UO_2$ and $U_3O_8$ particles. Thus, that method of producing uranium oxide powders is complex.

Currently, no method is known that can control a reaction from an accurate determination of the progress of a chemical conversion reaction in a furnace to obtain uranium oxides at the furnace outlet with the desired composition, and in particular uranium oxides with a high O/U ratio, i.e., oxides with a mean formula of the type $UO_{2+x}$, where x is relatively high (x in the range 0.03 to 0.7, preferably in the range 0.05 to 0.25).

More generally, when a chemical reaction is carried out between a substance in a condensed state, for example a solid powdered substance moving continuously in the longitudinal direction of a furnace, and a reactive gas mixture, no method is known for accurately determining the extent of the reaction at different points along the longitudinal direction of the furnace, and no method is known for controlling the reaction in the furnace from any such accurate determination.

An accurate determination of the extent of the reaction in the furnace must be carried out without opening the furnace and without risking the introduction of air into the furnace interior, since that would both completely falsify the measurements and analyses carried out, and would also modify the product being produced in the furnace. Thus, it is not possible to monitor the extent of the reactions by removing samples of the moving powdered substance at different points along the axis and inside the furnace chamber.

SUMMARY

The aim of the invention is to provide a method of determining the progress of at least one chemical reaction along the longitudinal direction of a furnace, the reaction taking place inside a chamber of the furnace between a reactive gas mixture and a substance in a condensed state, for example a powdered solid, in continuous movement in the longitudinal direction of the furnace, said method allowing the extent of the reaction and the progress of the chemical reaction in the longitudinal direction of the furnace to be determined in a precise and accurate manner, without needing to open the furnace and without modifying the progress of the chemical reaction while implementing the method.

To this end, a plurality of samples of the gas mixture are removed at a plurality of reference points spaced apart from one another along the longitudinal direction of the furnace, each of the gas samples is examined outside the furnace to determine the composition of the gas mixture, and the extent of the at least one chemical reaction is deduced from the composition of the gas mixture at each point.

The invention also provides a method of controlling at least one chemical reaction in a furnace to obtain a final product with a predetermined composition by using a prior determination of the progress of the chemical reaction in the longitudinal direction of the furnace to model the operation of the furnace. The chemical reaction is then controlled by injecting gases with a carefully selected composition and with a predetermined flow rate at least one point into the interior of the furnace chamber.

BRIEF DESCRIPTION OF THE DRAWINGS

In order to understand the invention, reference is now made to the accompanying figures to illustrate carrying out the determination method and the control method of the invention, in the case of a rotary furnace for converting uranium oxyfluoride into uranium oxide.

DETAILED DESCRIPTION

Figure 1:
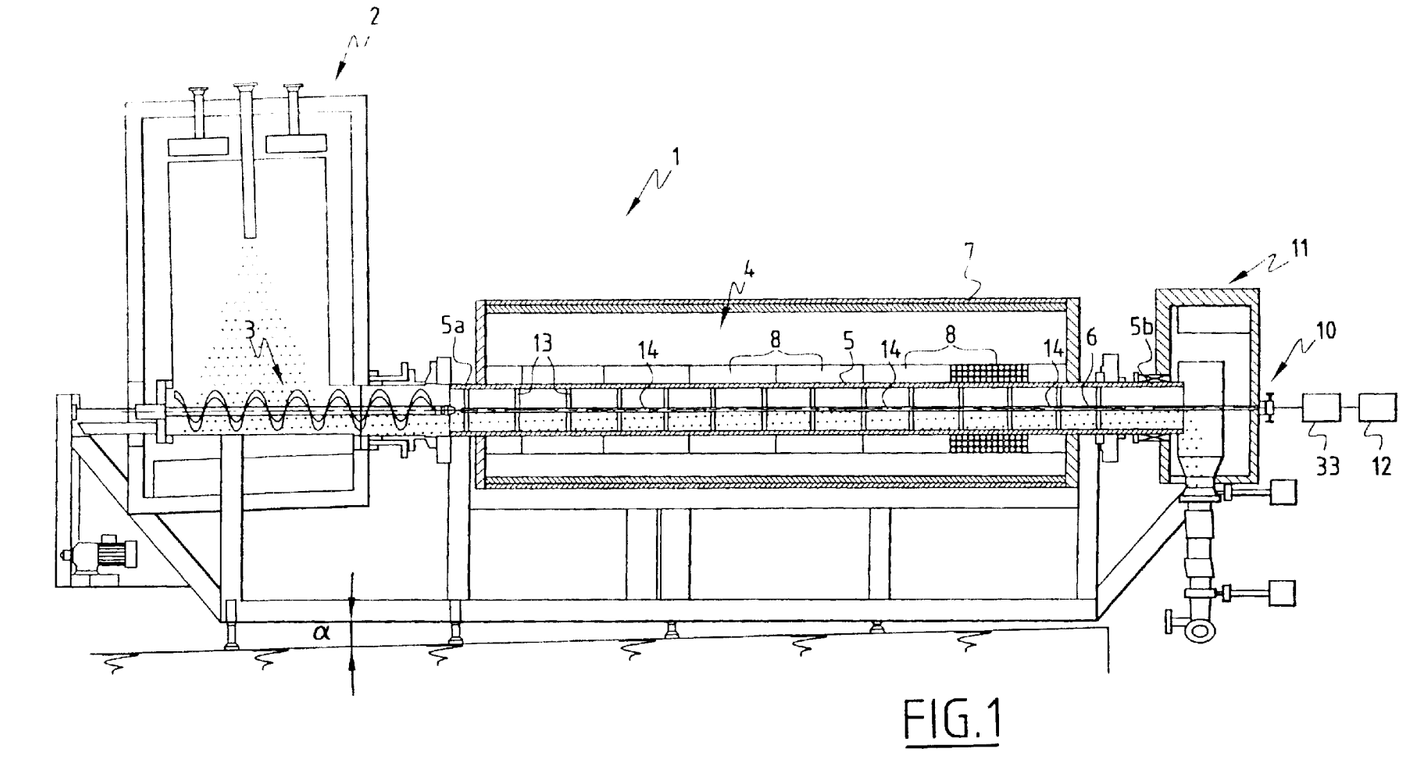
FIG. 1 is a longitudinal section through a unit for converting uranium hexafluoride into uranium oxide, comprising a rotary furnace provided with a sampling and injection apparatus that enables the methods of the invention to be carried out.

FIG. 1 illustrates a unit for converting uranium hexafluoride into uranium oxide, the unit being generally designated by the reference numeral 1 and comprising a reactor 2 for converting uranium hexafluoride $UF_6$ into uranium oxyfluoride $UO_2F_2$ by injecting gaseous hexafluoride $UF_6$, steam, and nitrogen into the reactor 2.

Uranium hexafluoride $UF_6$ is transformed into the oxyfluoride $UO_2F_2$ by oxidation in steam in accordance with the reaction:

$$UF_6 + 2H_2O \rightarrow UO_2F_2 + 4HF$$

The uranium oxyfluoride $UO_2F_2$ produced by the reaction is in the form of a powder that falls into the bottom of the reactor where this powder is taken up by a screw conveyor 3 for introduction into the inlet portion of a rotary furnace 4 inside which the uranium oxyfluoride powder is converted into uranium oxide.

The furnace 4 comprises a rotatably mounted tubular jacket 5 driven in rotation about a longitudinal axis 6, which is inclined at an angle $\alpha$ to the horizontal plane so that the inlet end 5a of the rotary jacket of the furnace is disposed at a higher level than the outlet end 5b.

Around the rotary furnace jacket inside an insulated chamber 7, heater elements 8 are disposed that heat the internal volume of the rotary jacket 5 in which the uranium oxyfluoride is transformed into uranium oxide at high temperature in accordance with the following reactions:

$$UO_2F_2 + H_2O \rightarrow UO_3 + 2HF \quad (1)$$

$$3UO_3 \rightarrow U_3O_8 + \tfrac{1}{2}O_2 \quad (2)$$

$$U_3O_8 + 2H_2 \rightarrow 3UO_2 + 2H_2O \quad (3)$$

$$\tfrac{1}{2}O_2 + H_2 \rightarrow H_2O \quad (4)$$

$$U_3O_8 \rightarrow U_3O_7 \rightarrow U_4O_9 \rightarrow UO_2 \quad (5)$$

The steam and hydrogen required to carry out the conversion inside the rotary furnace are introduced into the internal volume of the rotary jacket 5, generally by an injection arrangement introduced via the outlet end 5b of the rotary jacket 5 of the furnace.

The uranium oxyfluoride powder $UO_2F_2$ introduced via the screw conveyor 3 into the inlet end 5a of the rotary jacket 5 is transported towards the outlet end 5b during rotation of the rotary furnace by dint of the slope $\alpha$ of the longitudinal axis of said jacket 5. Further, rotation of the furnace produces agitation and lifts the powder which then comes into intimate contact with the steam and hydrogen injected into the furnace jacket and which generally move as a countercurrent to the movement of the powder inside the rotary jacket.

The end 5b of the rotary jacket 5 opens into a chamber of a unit 11 for recovering and conditioning the uranium oxide powder formed in the furnace by conversion of the uranium oxyfluoride powder.

The different gases formed inside the furnace chamber by the reactions transforming the oxyfluoride into uranium oxides and in particular hydrofluoric acid HF are recovered with excess hydrogen and steam which have not been used up in the chemical reactions occurring in the furnace.

As explained above, one of the inherent problems with carrying out a dry type conversion process in a unit such as unit 1 arises from the fact that in general, no information is available regarding the progress of the conversion inside the furnace jacket and on the extent of the different reactions occurring in the axial direction 6 of the rotary furnace.

As is explained below, accurate knowledge of the progress of the chemical reactions inside the rotary furnace enables the reactions to be controlled by injecting reactive gases and in particular hydrogen inside the rotary furnace at predetermined locations to obtain a uranium oxide mixture with general composition $UO_{2+x}$, where x is fixed at a pre-determined value, i.e., with an O/U ratio that is much higher than 2 and fixed at a well determined value.

Up to now, different means have been used to influence the chemical reactions inside the furnace, in particular by controlling the heater elements to obtain an optimal temperature distribution inside the furnace jacket along a longitudinal direction 6, and by the use of baffles 13 fixed inside the furnace to encourage contact between the reactive gas mixture moving in the furnace and the powder during conversion.

Chemical reactions inside the rotary furnace may also be controlled by adjusting the flow rates of hydrogen and steam introduced via the outlet end 5b of the rotary jacket, generally via a fixed chamber of the uranium oxide powder recovery and conditioning unit. However, satisfactory control of the uranium oxides produced has never been achieved by adjusting the flow rates of the steam and hydrogen introduced via the outlet end of the furnace.

In accordance with the invention, the progress of the chemical reactions occurring inside the furnace is accurately determined using a rod 10 for sampling gas at different points distributed along the longitudinal direction 6 of the furnace, connected to a gas analyzer 12 outside the furnace.

The extent of the reactions listed above occurring inside the rotary furnace may be determined at each of the points in the furnace by measuring the proportion or partial pressure of the gases produced by the various reactions or involved in said reactions, in particular HF, $H_2$, or $H_2O$. In particular, the presence or absence of a gas at a reference point along the longitudinal direction 6 of the furnace shows whether a chemical conversion reaction is in progress or has been completed.

Before start-up of a conversion unit such as unit 1, a first modeling operation is carried out that consists in causing the unit to function under its normal production conditions and in removing the gases present in the furnace from a plurality of sampling points distributed along the longitudinal direction 6 of the rotary furnace, then analyzing these gases outside the furnace.

The results of the gas analyses at different points in the furnace are used to construct a model representing the progress of the different chemical reactions occurring along the length of the furnace.

After this first stage of modeling the operation of the rotary furnace, the results of the modeling are used to determine the injections required at different points in the furnace, in particular hydrogen injection to obtain a powder $UO_{2+x}$ with an optimum O/U ratio from the furnace outlet. In general, the O/U ratio is intended to be in the range 2 to 2.7, preferably in the range 2.10 to 2.25.

It is possible to envisage producing oxides with an O/U ratio that is as high as 2.66, which has only been possible until now by mixing $UO_2$ and $UO_3O_8$ oxides.

To remove and analyze the gases inside the furnace (and optionally to inject gas into the furnace production phase), a long rod 10 is used with a length that is at least equal to the axial length of the jacket 5 of the rotary furnace and which is introduced into the internal volume of the rotary jacket 5 via its outlet end 5b and is disposed along its longitudinal axial direction 6. At one end of the furnace, the rod 10 is fixed to the rotary jacket of the furnace via an outer end portion to a fixed portion such as the wall of the recovery chamber of the oxide powder recovery and conditioning unit 11.

The sampling rod is connected to one or more gas analyzers 12 at its end located outside the furnace and the chamber of unit 11.

The rod 10 disposed in the axial longitudinal direction 6 of the rotary furnace 5 is completely free with respect to the rotary portions of the jacket 5 and in particular with respect to the baffles 13 occupying a portion of the cross section of the rotary jacket 5 of the furnace.

In the embodiment illustrated, the sampling rod 10 has ten sampling points 14 distributed along its length, to remove samples at ten reference points of the internal volume of the rotary jacket 5, with a substantially constant spacing between two successive reference points.

Figure 2:
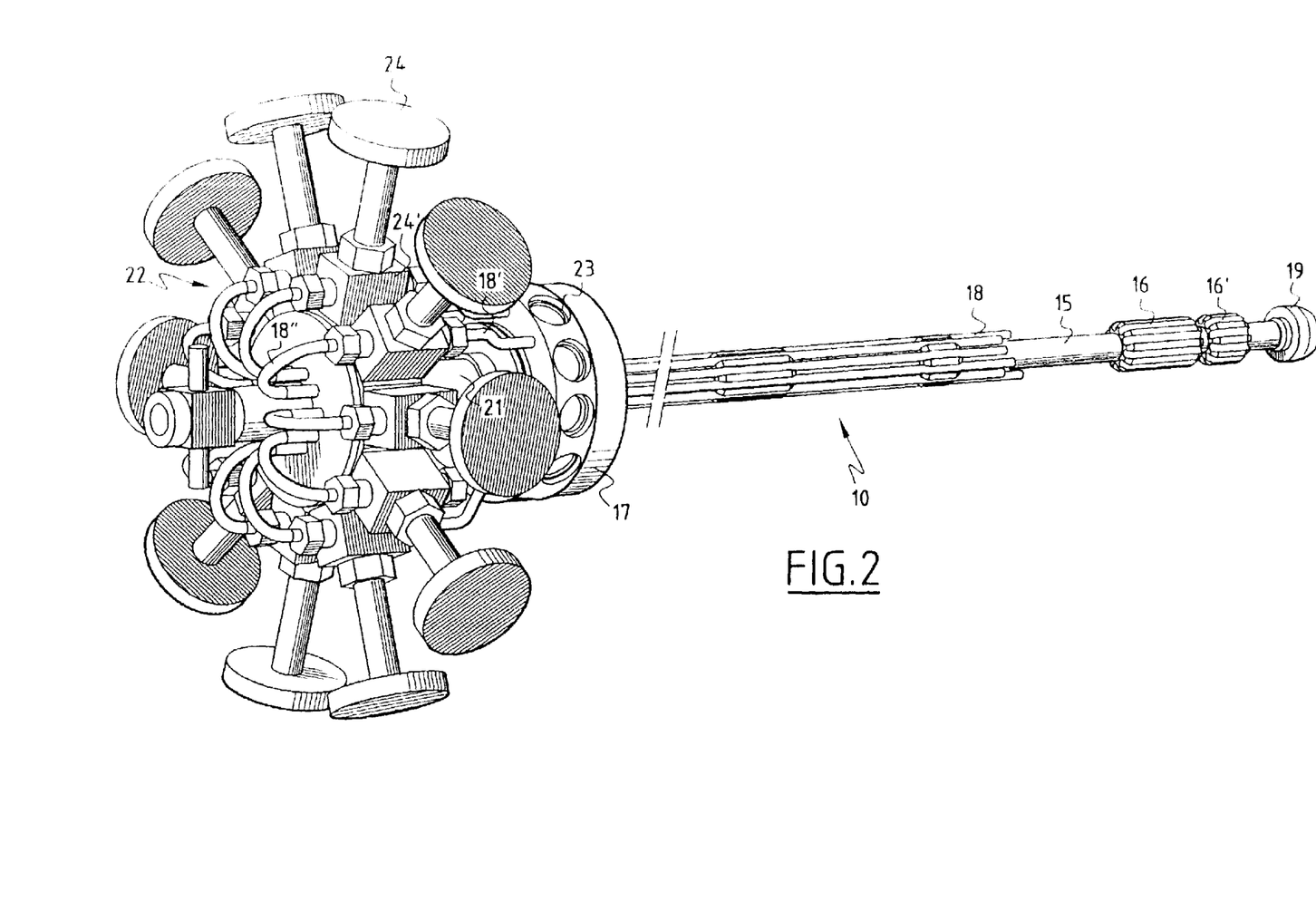
FIG. 2 is a perspective view of the sampling and injection apparatus of the invention.

Reference is now made to FIG. 2 to describe the sampling rod 10 assembly of the invention.

The sampling rod 10 comprises a long central tube 15 on which there are fixed, in a coaxial manner with predetermined spacing in the axial direction of the central support tube 5, support and guiding elements 16 and 16' which are primarily cylindrical in shape, each comprising, on its outer surface, a set of recesses each intended to receive one sampling tube 18 of a sampling tube assembly disposed parallel to the longitudinal axis of the central tube 15.

In the embodiment illustrated, each of the guiding and support elements 16 and 16' comprises ten recesses around its periphery in the shape of rectilinear channels of cross section having a semi-circular portion, machined into the support element 16 or 16'.

Fixed on the central tube 15, between two support elements 16 and equidistant from the two support elements 16, there is an intermediate support element 16' which is shorter in the axial direction than are the support elements 16.

The support elements 16' comprise a plurality of recesses of number and cross-section that are identical to those of the recesses in the longer support elements 16.

One axial end of the central tube 15 of the rod 10 is fixed to a flange 17 for connecting the rod 10 to the fixed wall of the unit 11, at the outlet from the rotary furnace.

The flange 17 has tapped openings for fixing the flange 17 and the rod 10 to the wall of the unit 11, so that the rod 10 is in a position that is coaxial with the jacket 5 of the rotary furnace, i.e., with the axis of its central tube 15 along the longitudinal axis 6 of the jacket 5 of the rotary furnace.

The end of the central tube 15 opposite from the end connected to the flange 17 is fixed to a pad 19 for closing the end of the central tube 15 which is inside the furnace, in a position close to the inlet end 5a of the rotary jacket 5.

The face of flange 17 that is opposite in the axial direction to the face thereof connected via an extension 21 to the central tube 15 of the rod is integral with a sampling assembly 22.

Each small diameter sampling tube 18 passes through a portion of the flange 17 in the axial direction, then is bent at 90° in a radial direction for connection, at the outer periphery of the flange 17, to an element 23 for connecting the tube 18 to an extension piece 18' that places the tube 18 in communication with a valve housing 24' of a valve 24 of the sampling apparatus 22.

Each valve housing 24' of a valve 24 of the sampling apparatus 22 is connected, via a curved connecting tube 18", to a sampling chamber machined in the housing of the sampling apparatus 22.

Each tube 18 may be placed in communication with the chamber of the sampling apparatus 22 via tubes 18' and 18" and a valve 24, 24'.

Each tube 18 extends in the axial direction of the rod 10 between the flange 17 and a sampling point 14 corresponding to a reference point inside the rotary furnace 4,5 at or near a short support and guiding element 16'.

Figure 3A:
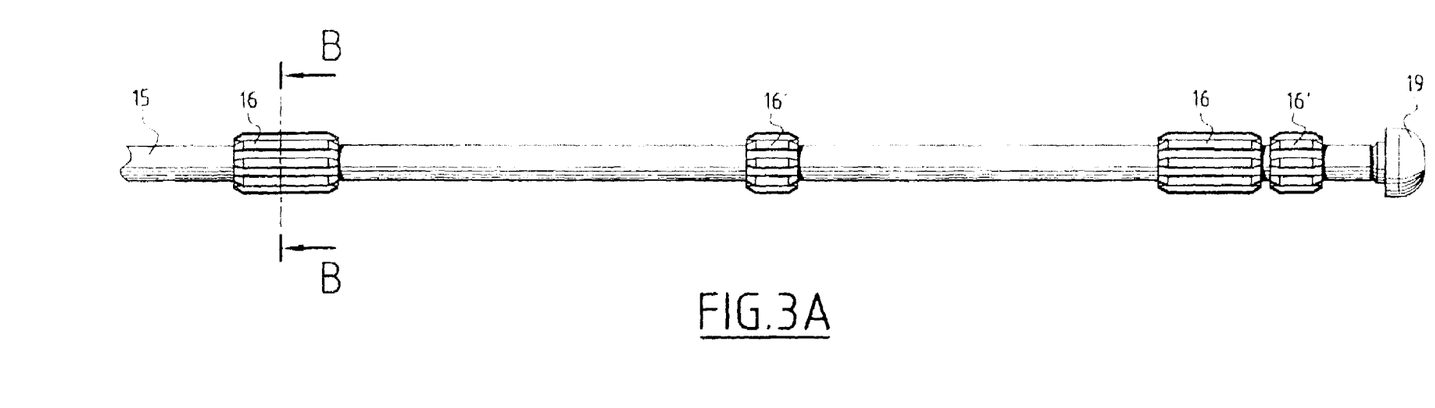
FIG. 3 is a view of a central support portion of a sampling rod of the apparatus shown in FIG. 2.

FIG. 3A illustrates the central tube 15 of the sampling rod 10 on which longer tube support and guiding elements 16 are fixed at regular intervals with shorter support and guiding elements 16' interspersed between the longer support and guiding elements 16.

A shorter guide element 16' intended to receive the last tube 18 that carries out the sampling at the last sampling point 14 located near the inlet end 5b of the rotary jacket of the furnace is fixed after the last longer guide element 16 on the end portion of the central tube 15 of the sampling rod 10, which is introduced into the rotary jacket of the furnace until it is close to the inlet end of the rotary jacket.

The end portion of the central tube 15 opposite to the end located near the inlet portion of the rotary jacket of the furnace has no support and guiding elements 16 or 16' along a section having an end which is intended to receive the flange 17 for fixing the sampling rod on the fixed structure of the unit.

The end portion of the rod comprising the end section of the central tube 15 that is free of guiding elements 16 and 16' is engaged through the chamber of the powder recovery and conditioning unit 11 and in the outlet portion of the rotary jacket 5 when the sampling rod 10 is fixed in its working position. In this portion of the sampling rod, the sampling tubes 18 located at the periphery of the central tube 15 are not fixed to the outer wall of the central tube 15.

Figure 3B:
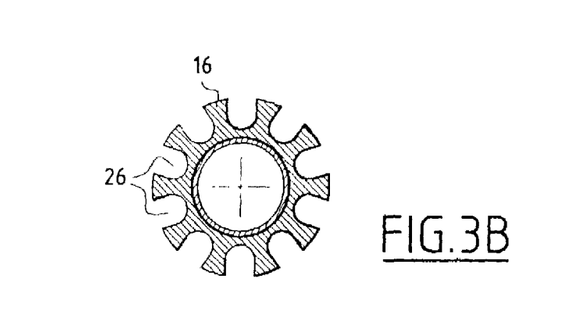

FIG. 3B is a cross-section through a support and guiding element 16 comprising ten recesses 26 each for receiving one sampling tube 18 and formed in the shape of channels with semi-circular bases extending in the axial direction over the peripheral surface of the support and guiding element 16 with a primarily cylindrical shape.

The section of the short support and guiding elements 16' is identical to the section of the longer support and guiding element 16 shown in FIG. 3B.

Figure 4:
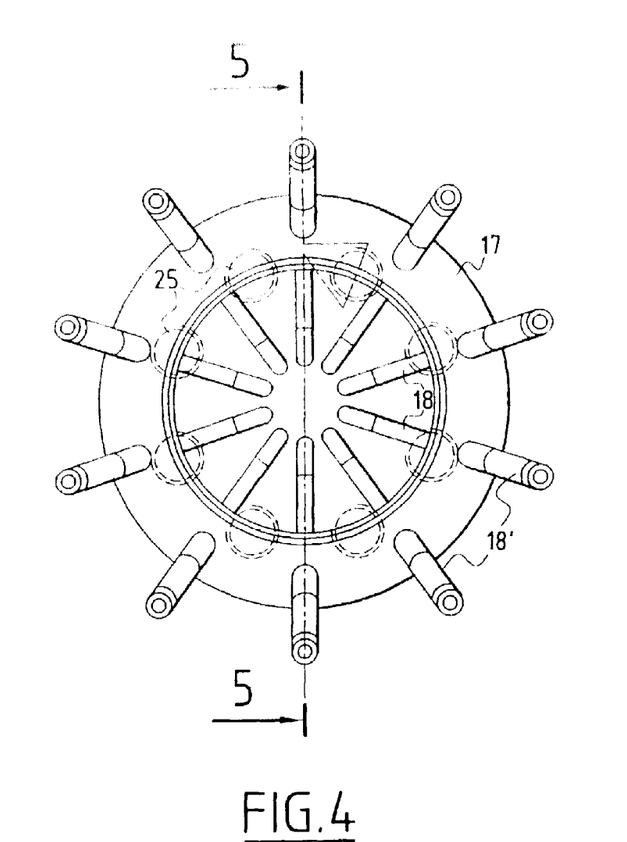
FIG. 4 is a front view of a flange of the sampling and injection apparatus shown in FIG. 2.
Figure 5:
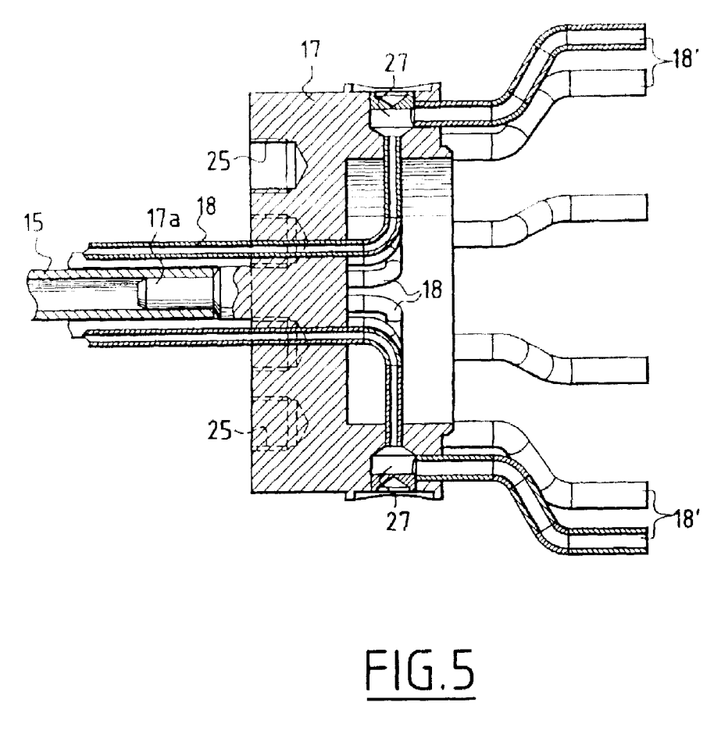
FIG. 5 is a cross-section on 5-5 of FIG. 4.

FIGS. 4 and 5 illustrate the flange 17 on which one end of the central tube 15 of the rod 10 is fixed and which forms the connection between the second end portions of the sampling tubes 18 and the extensions 18' of each of said sampling tubes.

One face of flange 17 in the axial direction comprises a projecting portion 17a on which the end of the central tube 15 is engaged and fixed by welding.

The sampling tubes 18 disposed about the central tube are each engaged in an opening passing through the axial direction of the flange 17 opening into a cylindrical cavity on the second face of the flange 17.

The openings for the tubes 18 through the flange 17 are disposed in the form of a circular array in the central portion of the flange 17 around the projecting portion 17a.

Tapped openings 25 for fixing the flange 17 onto a fixed portion of the conversion unit, for example on the wall of the chamber of the powder recovery and conditioning apparatus, are formed in the outer peripheral portion of the flange 17.

The end portion of the sampling tubes 18 is bent at 90° to place it in a radial direction with respect to the flange 17 and is engaged in an opening in the flange 17 opening into a chamber 27 for connecting the end of the sampling tube 18 with an S-shaped extension 18'.

A connecting chamber 27 is provided for each of the ten sampling tubes 18, around the outer periphery of the flange 17, each of the chambers 27 being closed by a plug.

The radially bent portion of the tube 18 and S-shaped extension 18' connect the sampling tubes surrounding the central tube 15 in a circular line of small diameter to the housings 24' of valves 24 of the sampling apparatus 22 disposed in a circular zone of diameter greater than the diameter of the flange 17.

Figure 6:
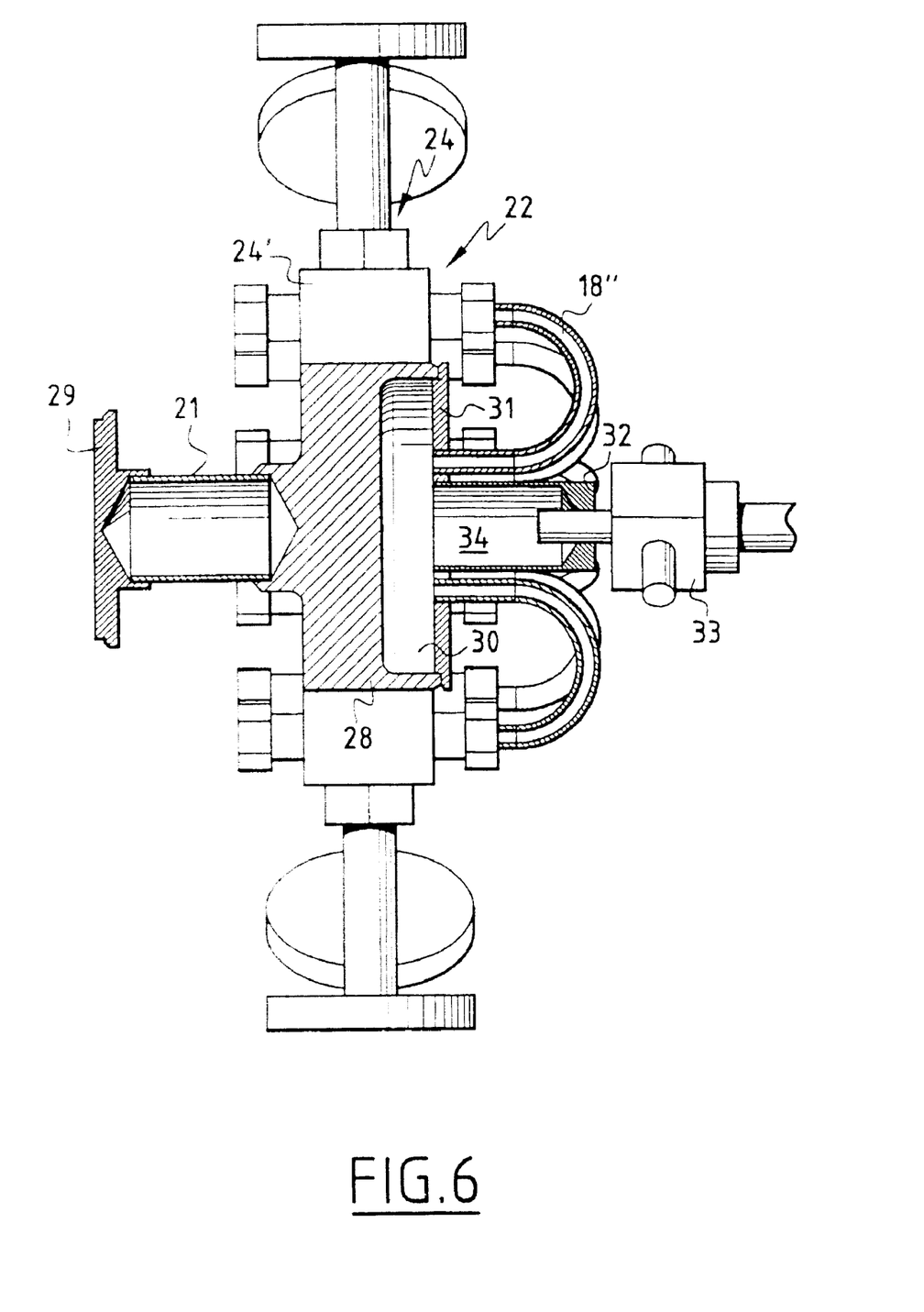
FIG. 6 is an axial section of a sampling and injection assembly of the apparatus shown in FIG. 2.

FIG. 6 illustrates that the sampling apparatus 22 comprises a housing of right prismatic shape 28 on which is fixed, in a coaxial disposition, the extension 21 that is integral with a plug 29 intended to be engaged in and fixed into the cavity machined on the second face of the flange 17. This provides the connection between the sampling apparatus 22 and the flange 17.

The sampling apparatus 22 comprises ten valves 24 having housings 24' which are fixed one after another in the circumferential direction around the housing 28, which preferably has a prismatic shape and a decagonal cross-section.

On the face opposite to the face connected to the connecting extension 21 of the flange 17, the housing 28 of the sampling apparatus 22 comprises a cavity 30 that is partially closed on the outer face of the housing 28 by an annular cover 31 with an internal bore that sealingly receives a tube 32 communicating with a connector 33 of the sampling apparatus. The cavity 30 has the smallest possible volume to reduce the inertia of the sampling system and to limit the risk of dilution of the mixture, and it constitutes a sampling chamber 34 with the internal space of the tube 32.

Each of the valve housings 24' of the valves 24 is connected to the sampling chamber 34 via a respective connection tube 18". One end of each bent connection tube 18" is connected to the housing 24' of a valve 24 and its second end is connected to an opening in the cover 31 closing the cavity 30. Each of the valve housings 24' of a valve 24 comprises a first chamber to which an extension tube 18' is connected and a second chamber to which a connection tube 18" is connected. When the valve 24 is closed, the two chambers are separated by the valve obturator, which may be a bellows-sealed valve. On opening valve 24, the two chambers of the valve housing and the sampling tube 18" are placed in communication with the sampling chamber 34 via the connection tubes 18' and 18".

Figure 7A:
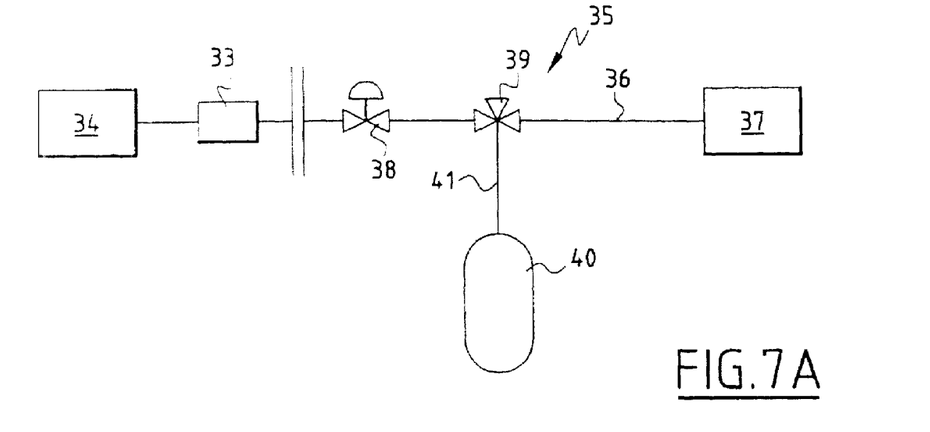
FIGS. 7A, 7B and 7C are diagrammatic views in three different functional positions of an analysis and purge circuit disposed outside the rotary furnace and connected to the sampling and injection apparatus of the invention.
Figure 7B:
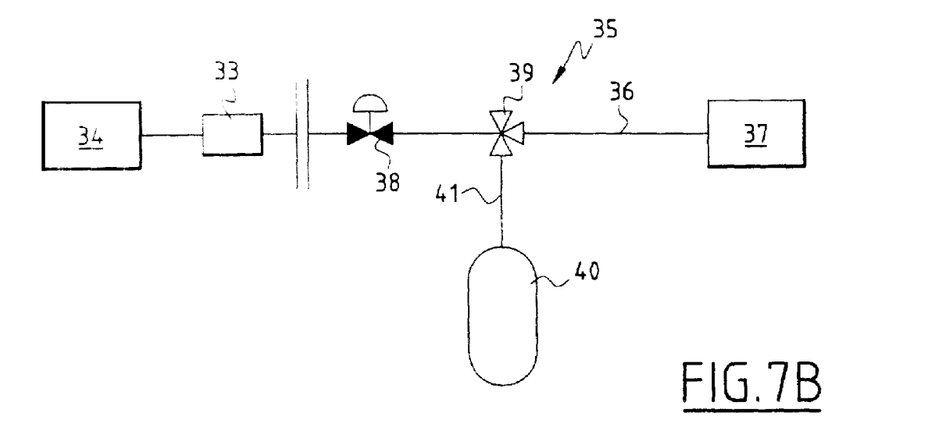
Figure 7C:
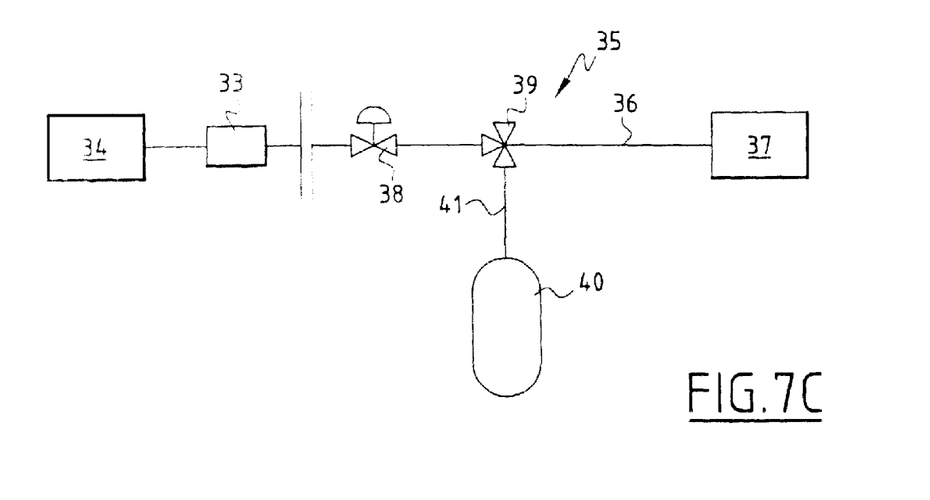

As may be seen in FIGS. 7A, 7B and 7C, the sampling chamber 34 is connected via the connector 33 to a gas purge, analysis, and injection circuit 35.

The circuit 35 comprises at least one line 36 connecting the connector 33 of the sampling chamber 34 and at least one gas analyzer 37, via a shut-off valve 38 and a three-port valve 39.

The three-port valve 39 has one port connected to the sampling chamber 34 via the connector 33 and a second port connected to the analyzer 37 via the line 36, and in a first position shown in FIG. 7A, it may place the sampling chamber in communication with the gas analyzer 37 when the shut-off valve 38 is open.

The principal sampling line 36 is connected via the third port of the three-port valve 39 to a side line 41 connected to a reservoir 40 that may contain an inert purge gas such as nitrogen, argon, or helium, or a reactive gas such as hydrogen.

As illustrated in FIG. 7B, when three-port valve 39 is placed in the position illustrated and the valve 38 is closed, analyzer 37 may be purged with purge gas from reservoir 40.

When three-port valve 39 is placed in its position shown in FIG. 7C and stop valve 38 is open, a purge gas may be sent into at least one of sampling tubes 18 via sampling chamber 34.

When reservoir 40 is a reservoir for a reactive gas such as hydrogen, the reactive gas may be sent into at least one sampling tube 18 via the sampling chamber 34, the three-port valve 39 being in its position shown in FIG. 7C and the shut-off valve 38 being open.

By actuating both the valves 24 of the sampling and distribution apparatus 22, which valves are preferably solenoid valves, and also the circuit valves 35, it is possible to purge the gas analyzer, purge any sampling tube 18 or a plurality of sampling tubes, or inject the reactive gases such as hydrogen into the rotary furnace of the conversion unit, at any reference point 14 or at a plurality of reference points in the furnace chamber.

As explained below, the apparatus described may make it possible to remove samples of gas at a plurality of points distributed along the longitudinal direction of the furnace and to analyze gas samples under very good conditions, enabling a graph of the progress of the chemical reactions in the furnace to be produced and thus providing a model of the furnace for the production of uranium oxide.

From a model of the oxide production furnace, it is possible to determine the injections of reactive gases, in particular hydrogen, required to obtain uranium oxide with a mean composition $UO_{2+x}$ with an O/U ratio of a desired value at the furnace outlet.

The reactive gases may be injected at one or more reference points in the furnace chamber each corresponding to a sampling point 14 by opening one or more valves 24 of the sampling and injection apparatus 22.

It is also possible to inject reactive gas at each reference point in the rotary furnace by opening all of the valves 24.

To carry out the gas sampling and analysis phase in the rotary furnace, the analyzer 37 is first purged with an inert gas then a first sampling line is purged. The reactive gas at the corresponding reference point 14 in the furnace is then sampled using the sampling tube, which has previously been purged. The gas samples are sent to the gas analyzer 37 which provides the composition of the sampled reactive gas mixture, i.e., the concentration or partial pressure of gases such as hydrofluoric acid HF and/or steam in the mixture and/or hydrogen and/or nitrogen.

To carry out an analysis of a sample that is perfectly representative of the atmosphere in the furnace in the sampling zone under consideration, it is necessary to ensure that the gas mixture is not modified by an internal reaction by deposition of substances or by condensation of the sampled gas.

To prevent further chemical reaction in a gas sample between the sampling point and the analyzer, the gas mixture is filtered at the inlet to the sampling tube by passing it through a metal filter made of a material that is resistant to the atmosphere of the furnace, for example a nickel alloy, to stop any solid material particles that may be in suspension in the gas sample. This prevents the chemical reaction from continuing by removing one component.

To avoid any condensation or deposition in the removed gas sample, the portions of the sampling tubes that are located outside the furnace and connected to the analyzer are heated. The valves 24 of the sampling apparatus 22 are also heated.

It is possible to use a single analyzer and thus a single line for moving the gas samples between the sampling apparatus 22 and the analyzer 37 or, in contrast, a plurality of analyzers connected to the sampling apparatus 22, each of the analyzers, for example, assaying one of the gases in the reactive gas mixture removed from the furnace.

Thus, in a first furnace modeling phase, the method and apparatus of the invention may remove gas samples from the furnace and analyze said gas samples, so that the result of the analyses is completely representative of the composition of the reactive gas mixture removed at the sampling points inside the furnace.

It is therefore possible to obtain a very accurate model of the rotary conversion furnace by determining the extent of the chemical conversion reactions at each of the furnace sampling points, more particularly the degree of completion of said chemical reactions. The model is in the form of graphs of the progress of the chemical reactions for forming oxides along the longitudinal direction of the furnace.

As an example, it is possible to monitor the concentration of HF or $H_2$ in the furnace in its longitudinal direction and to deduce the extent of the uranium oxyfluoride transformation reactions.

From the modeling of the furnace, it is possible to accurately determine the reference points in the furnace chamber where reactive gas such as hydrogen must be injected along with the rate at which it should be injected, and thus to steer the chemical reactions so as to obtain a uranium oxide with the desired mean composition at the furnace outlet.

This mean composition is then obtained without mixing oxide powders with different compositions, the powder leaving the furnace having the desired composition.

Further, injecting reactive gases directly into a zone of the furnace where said reactive gases are required may prevent a deficiency in the reactive gases, a disadvantage that arises when injecting reactive gases via the end of the rotary furnace. The reactive gases are not diluted by the furnace atmosphere and are introduced into the precise location where they have to be used, which limits the quantities of reactive gases used. Thus, the cost of producing uranium oxide is reduced.

The gases are removed from the furnace without using a suction or pumping arrangement because the pressure of the furnace exceeds that of the outer atmosphere. When a valve in the sampling apparatus is opened, the reactive gas then flows at high speed into the sampling tube 18 which is of section that is sufficiently small for the flow of the removed gas to remain very limited. In this way, samples are obtained of a composition that is entirely representative of the composition of the atmosphere in the furnace at the sampling points.

When converting uranium oxyfluoride into uranium oxide, assaying hydrogen in the samples may in particular allow determination of where and by how much the oxide $UO_2$ is being formed by reduction. It is then possible to influence the reactions to displace the point for total transformation into $UO_2$ to modify the composition of the oxides and the O/U ratio.

Assaying the hydrofluoric acid HF in the samples allows the uranium oxyfluoride to oxide transformation to be monitored.

The invention is not limited to the embodiment described.

Thus, it is possible to sample and inject gas in the furnace using arrangements other than those described.

It is possible to remove samples of the furnace atmosphere and to inject gas at any number of points. As an example, it is possible to implement the invention in a uranium oxyfluoride conversion furnace by injecting at five points of the ten sampling points.

The nature and flow rates of the injected gases depend on the nature of the chemical reactions occurring in the furnace and on the flow rates of the moving substances.

The invention is not limited to furnaces for converting uranium oxyfluoride into uranium oxide but may encompass applications in a plurality of furnaces in which a substance moves in its dense form, for example a powder, a paste or even a liquid form, which comes into contact with a reactive gas mixture and which therefore undergoes transformations in said furnace by chemical reactions.

The invention is also applicable outside the field of powder production for the manufacture of nuclear fuel.

What is claimed is:

1. A method of determining progress of at least one chemical reaction along a longitudinal direction of a furnace, the at least one chemical reaction taking place inside a chamber of a furnace between a reactive gas mixture and a substance in a condensed state in continuous movement in the longitudinal direction of the furnace comprising:
   removing a plurality of samples of the gas mixture at a plurality of reference points spaced apart from one another along the longitudinal direction of the furnace;
   analyzing each of the gas samples outside the furnace to determine a composition of the gas mixture; and
   deducing an extent of the at least one chemical reaction from the composition of the gas mixture at each point wherein the at least one chemical reaction is from contacting uranium oxyfluoride in a powder form moving in the furnace which is rotary with the reactive gas mixture to convert the uranium oxyfluoride into uranium oxides and the deducing the extent of the at least one chemical reaction is from the composition of the gas mixture at each of the reference points to obtain a model of the furnace in a form of graphs of a progress of uranium oxide formation reactions in the longitudinal direction of the furnace.

2. The method according to claim 1, further comprising: determining a concentration of hydrofluoric acid in the gas samples removed from the rotary furnace.

3. The method according to claim 1, further comprising: determining a concentration of at least one of hydrogen, nitrogen and steam gases in the gas samples removed from the rotary furnace.

4. A method of controlling a conversion of uranium oxyfluoride in a powder form moving in a longitudinal direction of the rotary furnace wherein the uranium oxyfluoride is in contact with a reactive gas mixture to convert the uranium oxyfluoride into uranium oxides comprising:
   producing a model of a rotary furnace in a form of graphs of a progress of uranium oxide formation reactions in the longitudinal direction of the furnace by deducing an extent of at least one chemical reaction from a composition of the gas mixture at reference points; and
   injecting the reactive gas mixture with at least one reactive gas into the rotary furnace at least one reference point defined from the model by a flow rate of the furnace model and physical properties of the gas to obtain uranium oxides with a mean composition of and with a predetermined O/U ratio at an outlet of the rotary furnace.

5. The method according to claim 4, wherein the predetermined O/U ratio of the uranium oxides at the outlet from the rotary furnace is in a range of 2 to 2.7.

6. The method according to claim 4, wherein the predetermined O/U ratio of the uranium oxides at the outlet from the rotary furnace is in a range of 2.10 to 2.25.

7. An assembly comprising a rotary furnace for converting uranium oxyfluoride in a powder form moving in a longitudinal direction of the furnace into uranium oxides by contacting the uranium oxyfluoride with a gas mixture, said assembly also comprising: an apparatus for carrying out a method for determining progress of the conversion of uranium oxyfluoride along the longitudinal direction of the furnace, said apparatus comprising:
   a sampling and injection rod comprising a central support tube;
   an arrangement configured to fix the central support tube inside the furnace in a disposition parallel to the longitudinal direction of the furnace;
   a plurality of sampling tubes positioned parallel to an axis of the central support tube distributed around a periphery of the central support tube; and
   a sampling device disposed outside the furnace connected to at least one gas analyzer, each of the sampling tubes comprising a first end opening into the furnace at a sampling point and a second end connected to the sampling device having valves to connect one of, in succession and in a grouped manner, each of the sampling tubes to the at least one analyzer wherein the sampling rod is fixed to one end of the rotary furnace, said first ends of the sampling tubes being distributed along the longitudinal direction of the furnace whereby an extent of the conversion of uranium oxyfluoride can be deduced from the composition of the gas mixture at the first ends of the sampling tubes.

8. The assembly according to claim 7, further comprising:
   a plurality of support and guiding elements with a generally cylindrical shape are fixed in a coaxial disposition around the central support tube at positions spaced along the axis of the central support tube, each of the support and guiding elements comprising a plurality of recesses each intended for one sampling tube of the plurality of sampling tubes.

9. The assembly according to claim 7, wherein the sampling device disposed outside the furnace comprises:
   a housing connected to the central tube of the sampling rod via an element for fixing the sampling rod inside the furnace, a sampling chamber configured in the housing of the sampling device; and
   a plurality of valves distributed around the housing of the sampling device each valve comprising a chamber in two parts separated from each other by an obturator of the valve, the sampling tubes each connected at a second end to a first chamber of a valve housing and a connector tube connecting a second chamber of the valve housing to the sampling chamber, the sampling chamber connected to the at least one analyzer via at least one line configured with at least one valve.

10. The assembly according to claim 9, wherein the sampling chamber of the sampling device is connected to the at least one analyzer via a line comprising in succession, between the chamber and the at least one analyzer, a shut-off valve and a three-port valve having one port connected to a portion of the line communicating with the sampling chamber, a second port connected to a portion of the line connected to the at least one analyzer and a third port connected to a reservoir containing one of an inert purge gas and a reactive gas.

11. The assembly according to claim 7, further comprising:
   a filter placed at an end of each of the sampling tubes, the filter configured to stop condensed substances and configured to stop the at least one chemical reaction in the sampling tube between the sampling point and the at least one analyzer.

12. The assembly according to claim 7, further comprising:
   an arrangement to heat the sampling tubes and valves of the sampling device to prevent condensation of a gaseous substance in the sampling tubes between the sampling points and the at least one analyzer.

13. The assembly according to claim 7, wherein the arrangement for fixing the central tube of the sampling rod is configured with a flange configured to allow passage for each of the tubes for connection to the sampling device.

* * * * *